United States Patent [19]

Takase et al.

[11] Patent Number: 5,432,078
[45] Date of Patent: Jul. 11, 1995

[54] **THERMOSTABLE STRAINS OF THE GENUS *THERMUS* CAPABLE OF PRODUCING A β LACTOSIDASE**

[75] Inventors: Mitsunori Takase, Oomiya; Kouki Horikoshi, Tokyo, both of Japan

[73] Assignees: Research Development Corporation of Japan, Tokyo; Kenkyusho, Rikagaku, Saitama; Morinaga Milk Industry Co., Ltd., Tokyo, all of Japan; a part interest

[21] Appl. No.: 142,128

[22] Filed: Oct. 28, 1993

Related U.S. Application Data

[60] Division of Ser. No. 744,110, Aug. 9, 1991, Pat. No. 5,283,189, which is a continuation-in-part of Ser. No. 153,296, Feb. 5, 1988, abandoned.

[30] Foreign Application Priority Data

Feb. 9, 1987 [JP] Japan .................... 62-26216

[51] Int. Cl.$^6$ .......................... C12N 1/20; C12P 19/14
[52] U.S. Cl. ............................. 435/252.1; 435/99; 435/170; 435/207; 435/822
[58] Field of Search ................ 435/14, 29, 41, 99, 435/170, 183, 207, 252.1, 822, 832

[56] References Cited

U.S. PATENT DOCUMENTS

| | | | |
|---|---|---|---|
| 4,442,214 | 4/1984 | Morgan et al. | 435/253 |
| 4,861,718 | 8/1989 | Hirata et al. | 435/207 |
| 4,895,801 | 1/1990 | Kan et al. | 435/101 |
| 5,283,189 | 2/1994 | Takase et al. | 435/207 |

FOREIGN PATENT DOCUMENTS 56-154991  11/1981  Japan .

OTHER PUBLICATIONS

Japanese Abstract 56-154991, beta–Galactosidase, Nov. 1981, Kaoru Fukuda, p. 1—complete ref. on order.
Journal of Bacteriology, May 1972, pp. 691–698, 1972, "Induction and Characterization of β-Galactosidase . . . ", Ulrich et al.

Primary Examiner—David M. Naff
Assistant Examiner—Deborah K. Ware
Attorney, Agent, or Firm—Nixon & Vanderhye

[57] ABSTRACT

Biologically pure strains of Thermus sp. FERM BP-1678, FERM BP-1679 and FERM BP-1680 have been isolated, and are capable of producing a beta-galactosidase. The beta-galactosidase produced by these strains has specific characteristics wherein the enzyme is optimum at a temperature of 75 to 85 degrees celsius and pH of 4.5 to 6.5. Further, the enzymatic activity is reduced by at most 10% in the presence of 50 millimoles (mM) of galactose and glucose, respectively.

3 Claims, 3 Drawing Sheets

THERMOSTABLE STRAINS OF THE GENUS *THERMUS* CAPABLE OF PRODUCING A β LACTOSIDASE

This is a divisional of application Ser. No. 07/744,110, filed Aug. 9, 1991, now U.S. Pat. No. 5,283,189 which is a continuation-in-part of Ser. No. 07/153,296 filed Feb. 5, 1988, now abandoned.

BACKGROUND OF THE INVENTION

1. Field of the Invention

This invention relates to a new strain belonging to genus Thermus which produces a new β-galactosidase, a new β-galactosidase and a process for producing the same.

2. Prior Art

β-galactosidase is an enzyme which decomposes lactose into glucose and galactose, and is used for the production of foods such as lactose-hydrolyzed milk, lactose-hydrolyzed solution, etc. The β-galactosidase widely exists in from animals and plants to microorganisms such as fungus, yeast, bacterium, etc., and enzymes which are now used in the food industry are relatively less thermostable β-galactosidases mainly derived from fungus or yeast. These β-galactosidases are disclosed in the official gazette of Jap. Pat. Pubin. No. 24094/1978 (Precedent 1) and the official gazette of Jap. Pat. Appln. Laid-open (Kokai)No. 44287/1977 (Precedent 2).

On the other hand, thermostable β-galactosidases are disclosed in Biotechnology and Bioengineering [vol. 26, p. 1141 (1982)] (Precedent 3), Journal of Applied Microbiology [vol. 2, p. 390 (1980)] (Precedent 4), Canadian Journal of Microbiology [vol. 22, p. 817 (817)] (Precedent 5), the official gazette of Jap. Pat. Appln. Laid-open (Kokai) No. 154991/1981 (Precedent 6) and Journal of Bacteriology [vol. 110. P. 691 (1972)] (Precedent 7). However, these conventional β-galactosidases all have one or more disadvantages such as low thermostability, narrow range of optimum pH and the inhibition of enzymatic action by a reaction product, as will be described later (see Table 2). Thus, the fact is that the conventional β-galactosidases are not put into practical use.

3. Problems to be Solved by the Invention

As described above, β-galactosidases now used for the production of foods on an industrial scale are relatively less thermostable enzymes, so that the lactose decomposition treatment is carried out generally at 55° C. or less. In addition, milk or lactose solution as a raw material is a preferable nutrition source for bacteria. As the result, the putrefaction owing to the saprophyte contamination during the treatment is a serious problem in the food production. Furthermore, an immobilized β-galactosidase results in its being insufficiently washed and sterilized after the completion of the production, as is also a serious problem in the food production. In order to solve these problems, the treatment of an object by using a thermostable β-galactosidase or the washing and the sterilization at a high temperature at which saparophytes are difficult to proliferate is desired, and the development of industrially applicable thermostable β-galactosidase is strongly demanded.

In order to meet such a demand, the search for the foregoing thermostable galactosidase had been attempted, and various thermostable β-galactosidases were found. However, there is no conventionally obtained thermostable β-galactosidase which has all of enzymological properties described in the following Items (1) to (3) required for the industrial use. That is, there is no thermostable β-galactosidase which attains the level of practical application:

(1) Having sufficient thermostability:
  Because the thermocoagulation of milk or defatted milk takes place at 78° to 80° C., it is desired that the enzymatic treatment is carried out at a temperature as higher as possible below said temperature. Thus, the enzyme is required to have a sufficient thermostability in the neighborhood of 70° to 75° C.

(2) Having an optimum pH in the range of neutrality to acidity:
  As raw materials to be treated with β-galactosidase, milk, defatted milk, cheese whey, lactose solution, etc. are assumed. These are raw materials in the neutral (pH 6.5) to acidic (pH 4.5) range, and thus are required to have sufficient enzymatic activities in said range.

(3) Low inhibition of enzymatic activity by reaction products:
  It is required that the lowering of the enzymatic activity by galactose and glucose as reaction products is small when β-galactosidase acts on lactose.

With an intention of creating a β-galactosidase having the properties described above, the present inventors tried to purely isolate a microorganism producing such a β-galactosidase from nature. As a result of it, they found that a microorganism belonging to genus Thermus as an extreme thermophille produced the β-galactosidase having the properties described above from among a large number of microorganisms producing β-galactosidase, and have completed the present invention.

SUMMARY OF THE INVENTION

An object of the present invention lies in providing a new microorganism producing a new β-galactosidase (hereinafter, referred to as "the present enzyme") having a high thermostability, an optimum pH in neutral to acidic range and an enzymatic activity which is not lowered by reaction products.

Another object of the present invention lies in providing the present enzyme and a process for producing the present enzyme.

That is, our invention contemplates to provide a new strain belonging to genus Thermus characterized by producing a new β-galactosidase having an optimum temperature of 75° to 85° C., an optimum pH of 4.5 to 6.5 and an enzymatic activity which is not lowered substantially by 50 mM each of galactose and glucose, a new β-galactosidase characterized by having an optimum temperature of 75° to 85° C., an optimum pH of 4.5 to 6.5 and an enzymatic activity which is not lowered substantially by 50 mM each of galactose and glucose and a new process for producing said new β-galactosidase characterized by culturing a strain belonging to genus Thermus producing a new β-galactosidase having an enzymatic activity which is not lowered substantially by 50 mM each of galactose and glucose and collecting said β-galactosidase.

According to the present invention, a β-galactosidase having a high thermostability, a wide action pH range and showing a low inhibition by reaction products can be obtained. That is, the present enzyme enables the treatment of lactose-contained foods such as milk, defatted milk, cheese whey, lactose solution, etc. at a high temperature at which the putrifaction by saprophytes is difficult to be caused. This effect makes the production process administration at the time of treating the foregoing foods simpler, as is very significant for the food industry.

DESCRIPTION OF THE PREFERRED EMBODIMENT (1) Acquisition of Microorganism

The present inventors isolated a large number of microorganisms known to produce β-galactosidases from soils collected from all parts of the country according to Bergey's Manual of Systematic Bacteriology (vol. 1; hereinafter referred to as "the manual"). Said microorganisms were cultured to produce β-galactosidases, and the produced β-galactosidases were isolated from media. As a result of studying their physicochemical properties, 3 strains producing the desired β-galactosidase, i.e., ZK-001, ZK-002 and ZK-003 were isolated. The identification of these strains according to the foregoing manual showed that they were all aerobic and asporogenic bacilli, immobile, gram-negative and catalase-positive and had a growth temperature of 40° to 80° C., an optimum growth temperature of 65° to 75° C. and an optimum growth pH around neutrality, wherefrom it was obvious that the strains were microorganisms belonging to genus Thermus. Furthermore, they are identified as novel strains according to the foregoing manual. The bacteriological properties of other three strains belonging to the genus Thermus, that is, those of Precedent 6, Precedent 7 and *Thermus aquaticus* ATCC 25104 (Type strain), are investigated according to the above described manual and compared with those of the present invention. The results are shown in Table 1. As evident from the Table 1, the strains of the present invention clearly differ from that of Precedent 6 in growth temperature and nitrate reduction. The growth temperature of the present strains is in the range of 40°–80° C., whereas that of Precedent 6 is 50°–85° C. In addition, the present strains reduce nitrates, that of Precedent 6 does not. The present strains also differ from that of Precedent 7 and *Thermus aquaticus* ATCC 2510 (Type strain) in the growth in s medium containing 2% NaCl. The present strains grow in a medium containing 2% NaCl, whereas that of Precedent 7 and *Thermus aquaticus* ATCC 25104 (Type strain) do not. In a further comparison, ZK-001 strain is different from Precedent 6 in assimilability of D-galactose and inositol. It also differs from Precedent 7 and *Thermus aquaticus* ATCC 25104 (Type strain) in assimilability of D-galactose. ZK-002 strain is different from Precedent 6 in assimilability of L-arabinose and D-mannitol, and from Precedent 7 and *Thermus aquaticus* ATCC 25104 (Type strain) in assimilability of L-arabinose, D-xylose and D-mannitol. ZK-003 strain is different from Precedent 6 in assimilability of inositol, and from Precedent 7 and *Thermus aquaticus* ATCC 25104 (Type strain) in gelatine liquefaction. As mentioned above, the microorganisms of the present invention are evidently distinct from those publicly known Thermus microorganisms. The present inventors deposited these strains on Feb. 6, 1987 under the terms of the Budapest Treaty on the International Recognition of the Deposit of Microorganisms for the Purposes of Patent Procedure at the Fermentation Research Institute; Agency of Industrial Science and Technology 1,3-Higashi 1-chrome, Tsukuba-shi, Ibaraki-ken Japan 305 and the strains where deposit numbers were given as follows: FERM BP-1678 (Bikoken-kinki No. 9184) for Thermus sp. ZK-001, FERM BP-1679 (Bikoken-kinki No. 9185) for Thermus sp. ZK-002 and FERM BP-1680 (Bikoken-kinki No. 9186) for Thermus sp. ZK-003.

TABLE 1

|  | *Thermus* sp. ZK-001 | *Thermus* sp. ZK-002 | *Thermus* sp. ZK-003 |
| --- | --- | --- | --- |
| 1. Morphological properties | | | |
| Shape | bacillus | bacillus | bacillus |
| Mobility | — | — | — |
| Gram's stain | — | — | — |
| Flagellum | — | — | — |
| Spore | — | — | — |
| 2. Growth on various media* | | | |
| Agar plate medium | circular, protuberant, orange | circular, protuberant, yellow | irregularly circular, flat, pale yellow |
| Agar slant medium | flat, orange | flat, yellow | flat, pale yellow |
| Liquid medium | grown cell mass precipitates | grown cell mass precipitates | grown cell mass precipitates |
| Litmus milk | no change | no change | no change |
| Liquid medium containing 5% NaCl | — | — | — |
| Liquid medium containing 2% NaCl | + | + | + |
| 3. Growth pH and temperature | | | |
| Growth pH | 5.5~8.5 | 5.5~8.5 | 5.5~8.5 |
| Growth temperature | 40~80° C. | 40~80° C. | 40~80° C. |
| 4. Biochemical properties | | | |
| Nitrate reduction | + | + | + |
| Denitrification reaction | ± | ± | ± |
| VP test | — | — | — |
| Indole formation | — | — | — |
| Hydrogen sulfide formation | — | — | — |
| Starch hydrolysis | ± | ± | ± |

TABLE 1-continued

|  | | | |
|---|---|---|---|
| Citric acid utilization | − | ± | − |
| Inorganic nitrogen source utilization | +(NH₄) | +(NH₄) | +(NH₄) |
| Coloring matter formation | formed (orange) | formed (yellow) | formed (pale yellow) |
| Urease | − | − | − |
| Oxidase | + | + | + |
| Catalase | + | + | + |
| O-F test | 0 | 0 | 0 |
| Oxygen requirement | Not grown under anaerobic condition | Not grown under anaerobic condition | Not grown under anaerobic condition |
| Gelatin liquefaction | − | − | + |
| 5. Assimilation of sugar | | | |
| L-arabinose | − | + | ± |
| D-xylose | − | + | ± |
| D-glucose | + | + | + |
| D-mannose | + | + | + |
| D-fructose | + | + | + |
| D-galactose | − | + | + |
| Maltose | + | + | + |
| Sucrose | + | + | + |
| Lactose | + | + | + |
| Trehalose | + | + | + |
| D-sorbitol | − | − | ± |
| D-mannitol | − | + | − |
| Inositol | − | + | − |
| Glycerin | − | − | − |
| Starch | − | − | − |

|  | Microorganism of Precedent 6 | Microorganism of Precedent 7 | *Thermus aquaticus* ATCC24104 (Type strain) |
|---|---|---|---|
| 1. Morphological properties | | | |
| Shape | bacillus | bacillus | bacillus |
| Mobility | − | − | − |
| Gram's stain | − | − | − |
| Flagellum | − | − | − |
| Spore | − | − | − |
| 2. Growth on various media* | | | |
| Agar plate medium | circular, protuberant, yellow | circular, protuberant, yellow | circular, protuberant, orange |
| Agar slant medium | flat, yellow | flat, yellow | flat, orange |
| Liquid medium | grown cell mass precipitates | grown cell mass precipitates | grown cell mass precipitates |
| Litmus milk | no change | no change | no change |
| Liquid medium containing 5% NaCl | − | − | − |
| Liquid medium containing 2% NaCl | + | − | − |
| 3. Grown pH and temperature | | | |
| Growth pH | 5.5~9.0 | 5.5~8.5 | 5.5~8.5 |
| Growth temperature | 50~85° C. | 40~80° C. | 40~80° C. |
| 4. Biochemical properties | | | |
| Nitrate reduction | − | + | + |
| Denitrification reaction | ± | ± | ± |
| VP test | − | − | − |
| Indole formation | − | − | − |
| Hydrogen sulfide formation | − | − | − |
| Starch hydrolysis | − | − | − |
| Citric acid utilization | − | ± | ± |
| Inorganic nitrogen source utilization | + | + | + |
| Coloring matter formation | formed (yellow) | formed (yellow) | formed (orange) |
| Urease | − | − | − |
| Oxidase | + | + | + |
| Catalase | + | + | + |
| O-F test | 0 | 0 | 0 |
| Oxygen requirement | Not grown under anaerobic condition | Not grown under anaerobic condition | Not grown under anaerobic condition |
| Gelatin liquefaction | ± | − | − |
| 5. Assimilation of sugar | | | |
| L-arabinose | − | − | − |
| D-xylose | ± | − | − |
| D-glucose | + | + | + |
| D-mannose | + | + | + |
| D-fructose | + | + | + |
| D-galactose | + | + | + |
| Maltose | + | + | + |
| Sucrose | + | + | + |

TABLE 1-continued

| | | | |
|---|---|---|---|
| Lactose | + | + | + |
| Trehalose | ± | + | + |
| D-sorbitol | − | − | − |
| D-mannitol | − | − | − |
| Inositol | + | ± | ± |
| Glycerin | − | − | − |
| Starch | − | − | − |

In Table 1, * means that media (pH 7.6) having the following composition were used as essential media, excluding litmus milk:

0.1% yeast extract, 0.1% tryptone, 10.0% inorganic salt solution (containing 1.0 g of nitrilotriacetic acid, 0.6 g of $CaSO_4.2H_2O$, 1.0 g of $MgSO_4.7H_2O$, 0.08 g of NaCl, 1.03 g of $KNO_3$, 6.89 g of $NaNO_3$ and 1.11 g of $Na_2HPO_4$ per liter of solution), 1.0% ferric chloride solution (containing 0.28 g of $FeCl_3.6H_2O$ per liter of solution), 1.0% trace element solution (containing 0.5 ml of $H_2SO_4$, 2.2 g of $MnSO_4.H_2O$, 0.5 g of $ZnSO_4.7H_2O$, 0.5 g of $H_3BO_3$, 0.016 g of $CuSO_4.5H_2O$, 0.025 g of $Na_2MoO_4.2H_2O$, and 0.046 g of $CoCl_2.6H_2O$), 0.001% thiamine hydrochloride, 0.001% nicotinamide, 0.001% biotin and 0.001% p-aminobenzoic acid.

(2) Acquisition of the Present Enzyme

Strains producing the present enzyme are inoculated on media which will be described later and aerobically cultured at 50° to 80° C., preferably at 65° to 75° C. for 12 to 48 hours.

The media contain inorganic salts, trace nutrients in addition to a carbon source and a nitrogen source according to demand. As a carbon source, various conventionally known materials can be used. For example, glucose, maltose, sucrose or soluble starch can be enumerated as typical examples. As a nitrogen source, there is also no restriction particularly. For example, organic nitrogen such as yeast extract, peptone, meat extract, corn steep liquor, amino acid solution, soybean meal, etc. or inorganic nitrogen such as ammonium sulfate, urea, ammonium nitrate, ammonium chloride, etc. can be enumerated as cheap and readily available sources. Incidentally, it goes without saying that the organic nitrogen source turns into a carbon source. Furthermore, in addition to such carbon and nitrogen sources as above, it is possible to add various salts in use commonly, e.g. inorganic salts such as magnesium salt, potassium salt, phosphate, iron salt, etc.; vitamin; etc. As a suitable medium, a liquid medium containing 0.2% glucose, 0.2% yeast extract, 0.2% tryptone, 10.0% inorganic salt solution (containing 1.0 g of nitrilotriacetic acid, 0.6 g of $CaSO_4.2H_2O$, 1.0 g of $MgSO_4.7H_2O$, 0.08 g of NaCl, 1.03 g of $KNO_3$, 6.89 g of $NANO_3$ and 1.11 g of $Na_2HPO_4$ per liter of solution), 1% ferric chloride solution (containing 0.28 g of $FeCl_3.6H_2O$ per liter of solution), 1.0% trace element solution (containing 0.5 ml of $H_2SO_4$, 2.2 g of $MnSO_4.H_2$, 0.5 g of $ZnSO_4.7H_2O$, 0.5 g of $H_3BO_3$, 0.016 g of $CuSO_4.5H_2O$, 0.025 g of $Na_2MoO_4.2H_2O$, and 0.046 g of $CoCl_2.6H_2O$), 0.001% thiamine hydrochloride, 0.001% nicotinamide, 0.001% biotin and 0.001% p-aminobenzoic acid and having a pH adjusted to 7.6 with NaOH can be enumerated.

The isolation and the purification of the present enzyme can be carried out, for example, as follows. Cell masses in a culture medium are collected by centrifugation, filtration, etc. and the obtained cell masses are disrupted in a buffer (e.g., 10 mM phosphate buffer of pH 7.0) in a usual way and then subjected to the extraction treatment. A supernatant of the resulting extract was applied to chromatography such as usual ion-exchange, gel filtration, etc., thereby obtaining the present enzyme.

A preferable method for acquiring the present enzyme can be exemplified as follows. Thermus sp. ZK-001 is inoculated, for example, into 5 l of such a medium as above and then aerobically cultured at 70° C. for 24 hours. The resultant culture is centrifuged at 12,000×g at 20° C. for 30 minutes so as to collect cell masses, thereby obtaining 55 g of cell mass.

To the obtained cell masses, are added approx. 300 ml of phosphate buffer (10 mM, pH 7.0) for extraction. Thus treated cell masses are disrupted in a mill so as to extract an enzyme. The obtained extract is centrifuged at 40,000×g for 60 minutes and the resulting supernatant is retained. Then, after extracting a precipitate by adding 200 ml of the above phosphate buffer for extraction, the obtained extract is centrifuged similarly and the supernatant is retained. Whereby, 480 ml of crude enzyme extract is obtained including the previously obtined supernatant. This crude enzyme solution is saturated to 60% by adding 187 g of ammonium sulfate thereto and then let stand overnight so as to form a precipitate. The precipitate is collected by centrifuging thus precipitated crude enzyme solution at 30,000×g for 60 minutes. The collected precipitate is dissolved in approx. 200 ml of 10 mM phosphate buffer (pH 7.0) and then dialyzed against said buffer. After discarding a precipitate in the dialyzed enzyme solution by centrifuging the solution at 40,000×g for 60 minutes, thus treated enzyme solution is loaded onto a column of DEAE-TOYOPEARL equilibrated with 10 mM phosphate buffer (pH 7.0). Then, the enzyme is eluted according to the concentration gradient method with 10 mM phosphate buffer (pH 7.0) containing 0 to 0.5M NaCl. The eluted active fractions are collected and concentrated with an ultrafilter, followed by dialyzing overnight using 10 mM phosphate buffer (pH 7.0) containing 0.1M NaCl. Thus treated enzyme solution is subjected to the gel filtration using a column of Sephacryl S-300 equilibrated with 10 mM phosphate buffer (pH 7.0) containing 0.1M NaCl to isolate 3 active fractions. The collected 3 active fractions are respectively dialyzed overnight using 10 mM phosphate buffer (pH 7.0) and then loaded onto columns of Sepharose 4B to which p-aminophenyl-β-D-thiogalactopyranoside equilibrated with said buffer is covalently bonded. After washing these columns thoroughly with 10 mM phosphate buffer (pH 7.0), 0.1M borate buffer is passed through the columns, whereby active fractions are eluted and isolated. Thus obtained 3 active fractions are respectively found to be purified to give single bands in the polyacrylamide gel electrophoresis (gel concentration: 7.5%, pH: 9.5). The yield of the obtained enzyme preparation amounts to 3.4 mg in total of 3 enzymatically active fractions and the activity yield thereof reaches 12%. Incidentally, with respect to other 2 strains, the present enzyme can be also obtained in the same manner described above while variously changing their culture conditions.

(3) Properties of the Present Enzyme

The enzymological properties of the present enzyme produced according to the present process are as follows:

A. Action: Hydrolyzing lactose into galactose and glucose.

B. Substrate specificity:
Hydrolyzing lactose, but not hydrolyzing sucrose, melibiose, raffinose and maltose.

Figure 1:
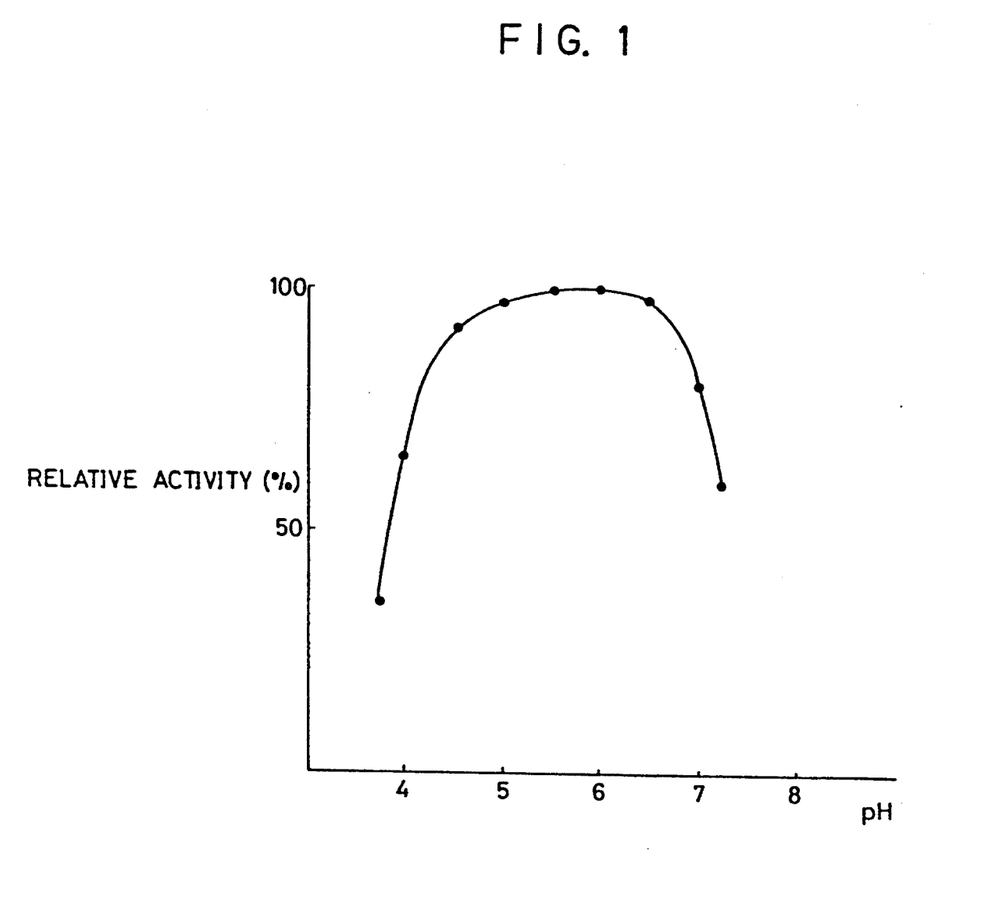
FIG. 1 is a graph showing the effect of pH on the present enzyme.

C. Optimum pH and stable pH range:
Optimum pH is 4.5 to 6.5. Stable within the pH range of 4.0 to 8.0 under the condition of 4hour retention at 55° C. (see the graph showing the effect of pH on the present enzyme activity in FIG. 1).

D. Thermostability:
At pH 7.0, 100% activity remains after 1-hour heating at 80° C. and 85% activity remains after 1-hour heating at 85° C.

Figure 2:
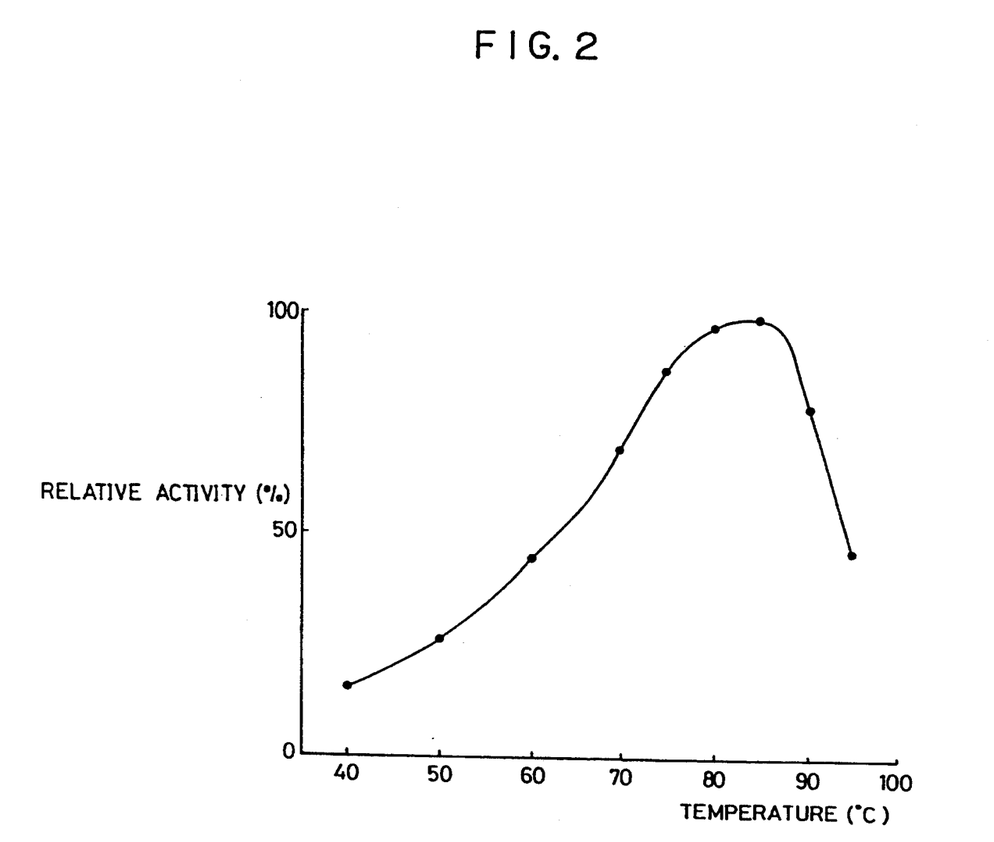
FIG. 2 is a graph showing the effect of temperature on the relatively activity of the present enzyme.

E. Optimum temperature range:
Having an optimum temperature within the range of 75° to 85° C. (see the graph showing the effect of temperature on the present enzyme activity in FIG. 2).

F. Effect of inorganic salts:
The enzymatic activity is not changed by 1 mM each of ferric chloride, manganese chloride, calcium chloride and magnesium sulfate, but is lowered by 1 mM each of zinc chloride and copper sulfate respectively by 10% and 30%.

G. Inhibition by reaction products:
The lowering of the enzymatic activity by 50 mM each of galactose and glucose is 10% or less (see the graph showing the inhibition of the present enzyme by reaction product in FIG. 3).

H. Molecular weight:
The determination of molecular weight of the present enzyme according to the gel filtration chromatography using Sephacryl S-3.00 column (1.6 cm × 100 cm) gives values corresponding to 55,000±5,000 dalton(monomer), 110,000±10,000 dalton (dimer) and 440,000±40,000 dalton(octamer).

The physicochemical and enzymological properties of the present enzyme and β-galactosidase derived from the conventionally known microorganisms (emzymes of the foregoing Precedent 1 to 6) are comparatively given in Table 2.

Incidentally, methods of measuring and indicating the activity are as follows.

That is, 0.1 ml of the present enzyme solution is added to 2.4 ml of 0.1M phosphate buffer (pH 6.5) containing 1.50% o-nitrophenyl-β-D-galactopyranoside (hereinafter referred to as "ONPG") and reacted at 70° C. for 10 minutes. Thereafter, the reaction is discontinued by the addition of 2.5 ml of 10% $Na_2CO_3$ solution. The amount of o-nitrophenol formed is obtained from the absorbance at 420 nm, and the amount of enzyme liberating 1 μmol of o-nitrophenol per minute is taken as one unit.

The inhibition by the reaction product was measured using as a substrate 1.50% ONPG containing 25 or 50 mM glucose or galactose. The other procedures are analogous with those used in the determination of β-galactosidase activity.

TABLE 2

|  | Present enzyme | Enzyme of Precedent 1 | Enzyme of Precedent 2 | Enzyme of Precedent 3 |
| --- | --- | --- | --- | --- |
| Strain | *Thermus* sp. | *Kluyveromyces lactis* | *Aspergillus oryzae* | *Thermus* strain 4-1A |
| Optimum temperature of enzymatic reaction | 75~85° C. | 40~50° C. | 50° C. | Not described |
| Thermostability of enzyme | 15% inactivation at 85° C. for 1 hr.; no inactivation at 80° C. for 1 hr. | 45% inactivation at 50° C. for 10 min. and 100% inactivation at 55° C. for 10 min. | 50% inactivation at 50° C. for 15 min. | 72% inactivation at 85° C. for 20 hr. and 25% inactivation at 75° C. for 20 min. |
| Optimum pH of enzymatic reaction | pH 4.5~pH 6.5 | pH 6~pH 7 | pH 4.5 | pH 6.0 |
| Inhibition by reaction product | 10% or less inhibition by 50 mM each of galactose and glucose | Not described | Not described | 52% inhibition by 56 mM of galactose and 63% inhibition by 56 mM of glucose |
| Molecular Weight (dalton) | 55,000 ± 5,000 110,000 ± 10,000 440,000 ± 40,000 | Not described | Not described | 440,000 |
|  | Enzyme of Precedent 4 | Enzyme of Precedent 5 | Enzyme of Precedent 6 | Enzyme of Precedent 7 |
| Strain | *Caldarilla acidophila* | *Bacillus stearothermophilus* | *Thermus thermophilus* | *Thermus aquaticus* |
| Optimum temperature of enzymatic reaction | 80° C. | 65° C. | 75~85° C. | 80° C. |
| Thermostability of enzyme | 50% inactivation at 85° C. for 55 hr. and 50% inactivation at 70° C. for 55 hr. | 60% inactivation at 60° C. for 10 min. | 20% inactivation at 90° C. for 20 min. and 5% inactivation at 85° C. for 20 min.; no inactivation at 80° C. for 150 min. | 55% inactivation at 90° C. for 30 min. and 28% inactivation at 80° C. for 30 min. |
| Optimum pH of enzymatic reaction | pH 5.0 | pH 6.0~pH 6.4 | pH 5.5~pH 6.5 | pH 5.0 |

TABLE 2-continued

| Inhibition by reaction product | No inhibition by 100 mM each of galactose and glucose | 20% inhibition by 10 mM of glucose and 71% inhibition by 10 mM of galactose | 26% inhibition by 50 mM of glucose and 21% inhibition by 50 mM of galactose | 59% inhibition by 50 mM of glucose and 36% inhibition by 50 mM of galactose |
|---|---|---|---|---|
| Molecular Weight (dalton) | Not described | 215,000 | 85,000 ± 5,000 | 570,000 |

Figure 3:
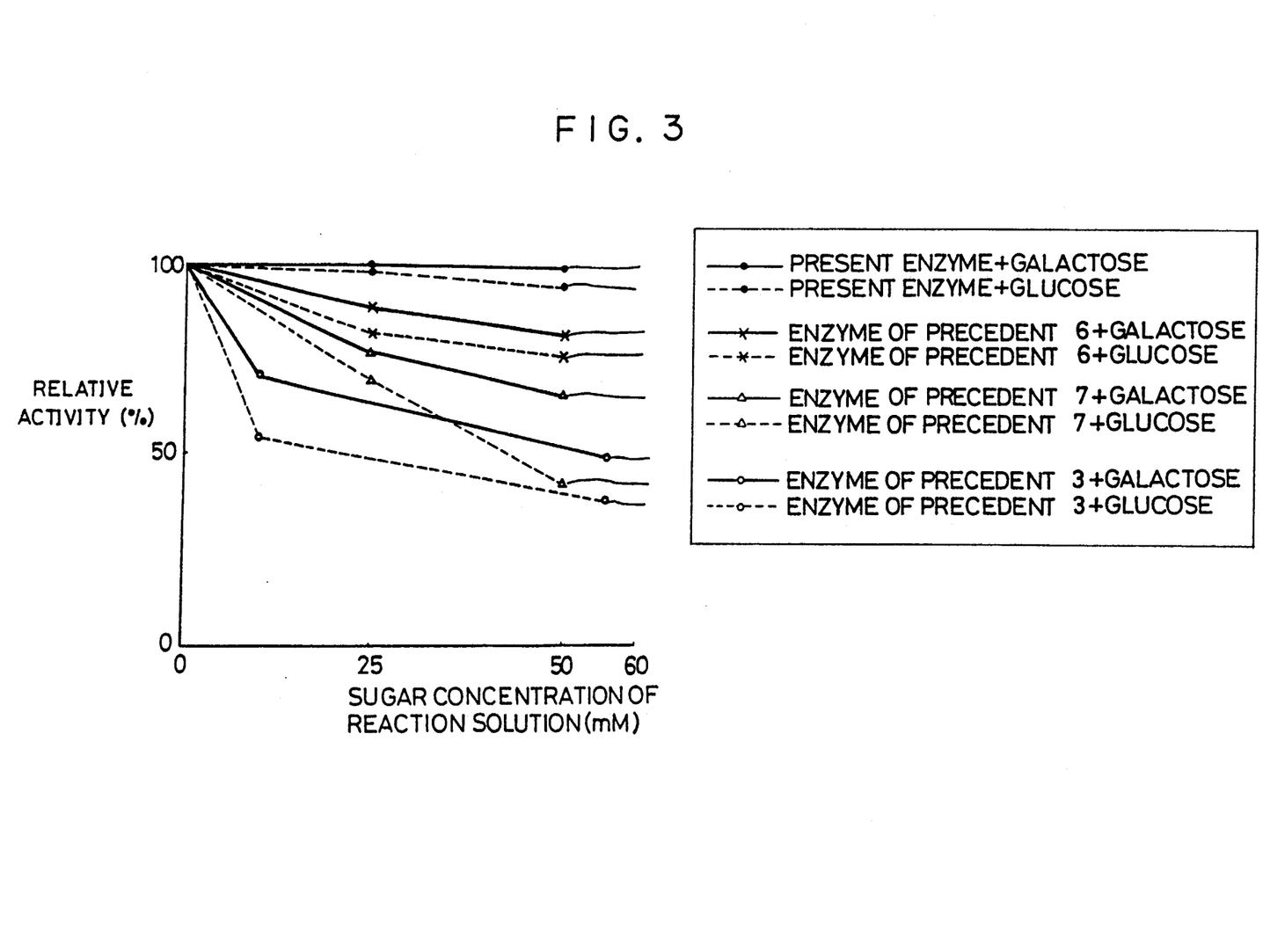
FIG. 3 is a graph showing the inhibition of the present enzyme by reaction products.

As shown in Table 2, the enzymological and physicochemical properties of the present enzyme are different from those of all the known β-galactosidases. The present enzyme unites properties of high thermostability, wide optimum pH range and low inhibition by reaction products. Especially, the galactosidase of the present invention greatly differs from the enzymes derived from the publicly known three strains (Precedents 3, 6 and 7) in the inhibition by the reaction product, as shown in FIG. 3, and therefore the enzyme of the present invention has more excellent properties in comparison with those of Precedents 3, 6 and 7. FIG. 3 is a graph showing the relative inhibition of various enzymes caused by the reaction product of each enzyme. In it, the relative reactivity is a percent over no or various sugar concentrations in the reaction solution. In this graph, the solid lines denote galactose and the broken lines glucose. More specifically, the solid line connecting the black circles represents the present enzyme+galactose and the broken line connecting the black circles represents the present enzyme+glucose; the solid line connecting the X's reports the enzyme of precedent 6+galactose and the broken line connecting the X's is the enzyme of precedent 6+glucose; the solid line connecting the deltas is the enzyme of precedent 7+galactose and the broken line connecting the deltas is the enzyme of precedent 7+glucose; and the solid line connecting the open circles is the enzyme of precedent 3+galactose and the broken line connecting the open circles is the enzyme of precedent 3+glucose. That is, the present enzyme posseses excellent properties which the conventional enzymes do not possess. Thus, the present enzyme is suitable for the high temperature processing of various lactose-contained foods such as milk, defatted milk, cheese whey, lactose solution, etc., and thus is industrially useful β-galactosidase.

Hereinafter, the present invention will be described more specifically, referring to examples. However, the present invention is nowise restricted to the examples given below.

EXAMPLE 1

Thermus sp. ZK-001 (FERM BP-1678) was inoculated into 10 l of liquid medium containing 0.2% glucose, 0.2% yeast extract, 0.2% tryprone, 10.0% inorganic salt solution (containing 1.0 g of nitrilotriacetic acid, 0.6 g of CaSO$_4$·2H$_2$O, 1.0 g of MgSO$_4$·7H$_2$O, 0.08 g of NaCl, 1.03 g of KNO$_3$, 6.89 g of NANO$_3$ and 1.11 g of Na$_2$HPO$_4$ per liter of solution), 1% ferric chloride solution (containing 0.28 g of FeCl$_3$·6H$_2$O per liter of solution), 1.0% trace element solution (containing 0.5 ml of H$_2$SO$_4$, 2.2 g of MnSO$_4$·H$_2$O, 0.5 g of ZnSO$_4$·7H$_2$O, 0.5 g of H$_3$BO$_3$, 0.016 g of CuSO$_4$·5H$_2$), 0.025 g of Na$_2$MoO$_4$·2H$_2$O, and 0.046 g of CoCl$_2$·6H$_2$O), 0.001% thiamine hydrochloride, 0.001% nicotinamide, 0.001% biotin and 0.001% p-aminobenzoic acid and having a pH adjusted to 7.6 with NaOH, and then cultured under aeration in a 20-l jar fermentor at 70° C. for 24 hours. The enzymatic activity of the culture solution was 0.84 unit/ml.

This culture solution was centrifuged at 12,000×g at 20° C. for 30 minutes so as to collect cell masses, thereby obtaining 107 g of cell mass. To the obtained cell masses, were added approx. 600 ml of phosphate buffer (10 mM, pH 7.0) for extraction. Thus treated cell masses were disrupted in a mill so as to extract an enzyme. The extract was centrifuged at 40,000×g for 60 minutes and the resulting supernatant was retained. Then, after extracting a precipitate by adding 400 ml of the above phosphate buffer for extraction, the extract was centrifuged similarly and the supernatant was retained. Whereby, 975 ml of crude enzyme extract was obtained including the previously obtained supernatant. This crude enzyme solution was saturated to 60% by adding 380 g of ammonium sulfate thereto and let stand overnight so as to form a precipitate. Then, the precipitate was collected by the centrifugation at 30,000×g for 60 minutes. The collected precipitate was dissolved in approx. 30 ml of 10 mM phosphate buffer (pH 7.0) and then dialyzed against said buffer. After eliminating a precipitate in the dialyzed enzyme solution by centrifuging the enzyme solution at 40,000×g for 60 minutes, the resulting enzyme solution was loaded onto a column (5 cm×45 cm) of DEAE-TOYOPEARL equilibrated with 10 mM phosphate buffer (pH 7.0). Then, the enzyme was eluted according to the concentration gradient method with 10 mM phosphate buffer (pH 7.0) containing 0 to 0.5M NaCl. 48.0 ml of eluted active fraction was concentrated to approx. 10 ml by using an ultrafilter (PM-10 manufactured by Amicon Corp.) and the resulting concentrate was dialyzed overnight using 10 mM phosphate buffer (pH 7.0) containing 0.1M NaCl. Thus treated enzyme solution was passed through a gel filtration column (2.6 cm×95 cm) of Sephacryl S-300 equilibrated with 10 mM phosphate buffer (pH 7.0) containing 0.1M NaCl to isolate 3 active fractions. Said 3 fractions were combined, dialyzed overnight using 10 mM phosphate buffer, and then loaded onto a column of Sepharose 4B to which p-aminophenyl-β-D-thiogalactopyranoside equilibrated with said buffer was covalently bonded. After washing this column thoroughly with 10 mM phosphate buffer (pH 7.0), 0.1M borate buffer was passed through the column to elute and isolate active fractions. As a result, approx. 8.5 mg of the present enzyme was obtained.

EXAMPLE 2

Thermus sp. ZK-002 was inoculated into 10 l of the same medium as in Example 1, except that 0.2% soluble starch was used instead of glucose. The culture was carried out under the same conditions as in Example 1, whereby 0.64 units/ml of culture solution was obtained. Hereinafter, the purification was carried out in the same manner as in Example 1, whereby approx. 6.8 mg of the present enzyme was obtained.

EXAMPLE 3

Thermus sp. ZK-003 was inoculated into 10 l of medium having the same composition as described in Example 1 and cultured under the same conditions as in Example 1, whereby 0.68 units/ml of culture solution was obtained. Hereinafter, the purification was carried out in the same manner as in Example 1, whereby approx. 7.3 mg of the present enzyme was obtained.

What is claimed is:

1. A biologically pure microorganism Thermus sp FERM BP-1678 which is capable of producing β-galactosidase having an optimum temperature of 75° to 85° C., an optimum pH of 4.5 to 6.5 and an enzymatic activity reduced by at most 10% by the presence of 50 mM each of galactose and glucose, said biologically pure microorganism having at least the following bacteriological properties:

| | | |
|---|---|---|
| A. | Morphological properties: | |
| | Shape | bacillus |
| | Mobility | − |
| | Gram's stain | − |
| | Flagellum | − |
| | Spore | − |
| B. | Growth on various media: | |
| | Agar plate medium | circular, protuberant, orange |
| | Agar slant medium | flat, orange |
| | Liquid medium | grown cell mass precipitates |
| | Litmus milk | no change |
| | Liquid medium containing 5% NaCl | − |
| | Liquid medium containing 2% NaCl | + |
| C. | Growth pH and temperature: | |
| | Growth pH | 5.5–8.5 |
| | Growth temperature | 40–80° C. |
| D. | Biochemical properties | |
| | Nitrate reduction | + |
| | Denitrification reaction | ± |
| | VP test | − |
| | Indole formation | − |
| | Hydrogen sulfide formation | − |
| | Starch hydrolysis | ± |
| | Citric Acid utilization | |
| | Inorganic nitrogen source utilization | +(NH4) |
| | Coloring matter formation | formed (orange) |
| | Urease | − |
| | Oxidase | + |
| | Catalase | + |
| | O-F test | 0 |
| | Oxygen requirement | Not grown under anaerobic condition |
| | Gelatin liquefaction | |
| E. | Assimilation of sugar: | |
| | L-arabinose | − |
| | D-xylose | − |
| | D-glucose | + |
| | D-mannose | + |
| | D-fructose | + |
| | D-galactose | − |
| | Maltose | + |
| | Sucrose | + |
| | Lactose | + |
| | Trehalose | + |
| | D-sorbitol | − |
| | D-mannitol | − |
| | Inositol | − |
| | Glycerin | − |
| | Starch | − |

2. A biologically pure microorganism Thermus sp FERM BP-1679 which is capable of producing β-galactosidase having an optimum temperature of 75° to 85° C., an optimum pH of 4.5 to 6.5 and an enzymatic activity reduced by at most 10% by the presence of 50 mM each of galactose and glucose, said biologically pure microorganism having at least the following bacteriological properties:

| | | |
|---|---|---|
| A. | Morphological properties: | |
| | Shape | bacillus |
| | Mobility | − |
| | Gram's stain | − |
| | Flagellum | − |
| | Spore | − |
| B. | Growth on various media: | |
| | Agar plate medium | circular, protuberant, yellow |
| | Agar slant medium | flat, yellow |
| | Liquid medium | grown cell mass precipitates |
| | Litmus milk | no change |
| | Liquid medium containing 5% NaCl | − |
| | Liquid medium containing 2% NaCl | + |
| C. | Growth pH and temperature: | |
| | Growth pH | 5.5–8.5 |
| | Growth temperature | 40–80° C. |
| D. | Biochemical properties | |
| | Nitrate reduction | + |
| | Denitrification reaction | ± |
| | VP test | − |
| | Indole formation | − |
| | Hydrogen sulfide formation | − |
| | Starch hydrolysis | ± |
| | Citric Acid Utilization | ± |
| | Inorganic nitrogen source utilization | +(NH4) |
| | Coloring matter formation | formed (yellow) |
| | Urease | − |
| | Oxidase | + |
| | Catalase | + |
| | O-F test | 0 |
| | Oxygen requirement | Not grown under an aerobic condition |
| | Gelatin liquefaction | − |
| E. | Assimilation of sugar: | |
| | L-arabinose | + |
| | D-xylose | + |
| | D-glucose | + |
| | D-mannose | + |
| | D-fructose | + |
| | D-galactose | + |
| | Maltose | + |
| | Sucrose | + |
| | Lactose | + |
| | Trehalose | + |
| | D-sorbitol | − |
| | D-mannitol | + |
| | Inositol | + |
| | Glycerin | − |
| | Starch | − |

3. A biologically pure microorganism Thermus sp FERM BP-1680 which is capable of producing β-galactosidase having an optimum temperature of 75° to 85° C., an optimum pH of 4.5 to 6.5 and an enzymatic activity reduced by at most 10% by the presence of 50 mM each of galactose and glucose, said biologically pure microorganism having at least the following bacteriological properties:

| | | |
|---|---|---|
| A. | Morphological properties: | |
| | Shape | bacillus |
| | Mobility | − |
| | Gram's stain | − |
| | Flagellum | − |
| | Spore | − |
| B. | Growth on various media: | |
| | Agar plate medium | irregularly circular, flat, pale yellow |
| | Agar slant medium | flat, pale yellow |

-continued

| | |
|---|---|
| Liquid medium | grown cell mass precipitates |
| Litmus milk | no change |
| Liquid medium containing 5% NaCl | − |
| Liquid medium containing 2% NaCl | + |
| C. Growth pH and temperature: | |
| Growth pH | 5.5–8.5 |
| Growth temperature | 40–80°C. |
| D. Biochemical properties: | |
| Nitrate reduction | + |
| Denitrification reaction | ± |
| VP test | |
| Indole formation | − |
| Hydrogen sulfide formation | − |
| Starch hydrolysis | ± |
| Citric acid utilization | − |
| Inorganic nitrogen source utilization | +(NH$_4$) |
| Coloring matter formation | formed (pale yellow) |
| Urease | − |
| Oxidase | + |
| Catalase | + |
| O-F test | 0 |
| Oxygen requirement | Not grown under anaerobic condition |
| Gelatin liquefaction | + |
| E. Assimilation of sugar: | |
| L-arabinose | ± |
| D-xylose | ± |
| D-glucose | + |
| D-mannose | + |
| D-fructose | + |
| D-galactose | + |
| Maltose | + |
| Sucrose | + |
| Lactose | + |
| Trehalose | + |
| D-sorbitol | ± |
| D-mannitol | − |
| Inositol | − |
| Glycerin | − |
| Starch | − |

\* \* \* \* \*